United States Patent
Blanc et al.

(10) Patent No.: US 12,009,102 B2
(45) Date of Patent: Jun. 11, 2024

(54) AUTOMATED SYSTEM FOR MONITORING A PATIENT'S BLOOD SUGAR

(71) Applicant: Commissariat à l'Énergie Atomique et aux Énergies Alternatives, Paris (FR)

(72) Inventors: Romain Blanc, Grenoble (FR); Eléonore Maeva Doron, Grenoble (FR); Hector-Manuel Romero Ugalde, Grenoble (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 765 days.

(21) Appl. No.: 17/055,097

(22) PCT Filed: May 3, 2019

(86) PCT No.: PCT/FR2019/051025
§ 371 (c)(1),
(2) Date: Nov. 12, 2020

(87) PCT Pub. No.: WO2019/224446
PCT Pub. Date: Nov. 28, 2019

(65) Prior Publication Data
US 2021/0268185 A1    Sep. 2, 2021

(30) Foreign Application Priority Data
May 22, 2018 (FR) .................................. 1800492

(51) Int. Cl.
G16H 50/00 (2018.01)
A61B 5/00 (2006.01)
(Continued)

(52) U.S. Cl.
CPC ......... *G16H 50/30* (2018.01); *A61B 5/14532* (2013.01); *A61B 5/1495* (2013.01);
(Continued)

(58) Field of Classification Search
CPC ...... A61M 2205/702; A61M 2230/201; A61M 5/1723
See application file for complete search history.

(56) References Cited

U.S. PATENT DOCUMENTS

| | | | |
|---|---|---|---|
| 2013/0211220 A1* | 8/2013 | Cobelli | G16H 20/17 600/365 |
| 2014/0276556 A1 | 9/2014 | Saint et al. | |

(Continued)

FOREIGN PATENT DOCUMENTS

| | | |
|---|---|---|
| JP | 2010-512945 A | 4/2010 |
| JP | 2012-502693 A | 2/2012 |
| JP | 2017-532113 A | 11/2017 |

OTHER PUBLICATIONS

Blanc et al. "Modeling the variability of insulin sensitivity for people with Type 1 Diabetes based on clinical data from an articificial pancreas study", 2019, IEEE Xplore, 10.1109/EMBC. 2019.8857170 (Year: 2019).*

(Continued)

*Primary Examiner* — William R Carpenter
(74) *Attorney, Agent, or Firm* — Wolf, Greenfield & Sacks, P.C.

(57) ABSTRACT

An automated system for controlling a patient's blood glucose, including a blood glucose sensor and a processing and control unit, wherein the processing and control unit is configured to calculate, from a first mathematical model $f_{CR}$ specific to the patient and taking into account a single blood glucose value $G^r$ measured by the sensor, a factor CR representative of the patient's insulin sensitivity.

10 Claims, 3 Drawing Sheets

(51) Int. Cl.
    *A61B 5/145*     (2006.01)
    *A61B 5/1495*     (2006.01)
    *A61M 5/172*     (2006.01)
    *G05B 13/04*     (2006.01)
    *G16H 10/60*     (2018.01)
    *G16H 20/17*     (2018.01)
    *G16H 40/40*     (2018.01)
    *G16H 40/67*     (2018.01)
    *G16H 50/20*     (2018.01)
    *G16H 50/30*     (2018.01)
    *G16H 50/70*     (2018.01)
    *G16H 20/60*     (2018.01)

(52) U.S. Cl.
    CPC ......... *A61B 5/4839* (2013.01); *A61M 5/1723* (2013.01); *G05B 13/048* (2013.01); *G16H 10/60* (2018.01); *G16H 20/17* (2018.01); *G16H 40/40* (2018.01); *G16H 40/67* (2018.01); *G16H 50/20* (2018.01); *G16H 50/70* (2018.01); *A61M 2205/702* (2013.01); *A61M 2230/201* (2013.01); *G16H 20/60* (2018.01)

(56) References Cited

U.S. PATENT DOCUMENTS

2015/0031053 A1*   1/2015   Moerman .......... G01N 33/6893
                                                                            435/7.92
2016/0089494 A1*   3/2016   Guerrini ................ G16H 20/17
                                                                            604/504

OTHER PUBLICATIONS

International Preliminary Report on Patentability for International Application No. PCT/FR2019/051025, dated Dec. 3, 2020.
International Search Report and Written Opinion for International Application No. PCT/FR2019/051025, dated Aug. 12, 2019.
Patarrão et al., Assessment of methods and indexes of insulin sensitivity. Revista Portuguesa de Endocrinologia, Diabetes e Metabolismo. Jan. 1, 2014;9(1):65-73.
Xin-Long et al., Insulin resistance following thermal injury: an animal study. Burns. Jun. 1, 2007;33(4):480-3.

\* cited by examiner

AUTOMATED SYSTEM FOR MONITORING A PATIENT'S BLOOD SUGAR

This application is a national stage filing under 35 U.S.C. § 371 of International Patent Application Serial No. PCT/FR2019/051025, filed May 3, 2019, which claims priority to French patent application FR18/00492, filed May 22, 2018. The entire contents of these applications are incorporated herein by reference in their entirety.

BACKGROUND

The present disclosure concerns the field of automated blood glucose control systems, and more particularly aims, in such a system, at the determination of a factor representative of the patient's insulin sensitivity.

DISCUSSION OF THE RELATED ART

Automated blood glucose regulation systems, also called artificial pancreases, enabling to automatically regulate the insulin inputs of a diabetic patient based on his/her blood glucose history, on his/her meal history, on his/her insulin injection history have already been provided, for example, in French patent application No. 1658881 (B15018/DD16959) filed on Sep. 21, 2016, in French patent application No. 1658882 (B15267/DD17175) filed on Sep. 21, 2016, and in French patent application No. 1756960 (B15860/DD18480) filed on Jul. 21, 2017.

The regulation systems described in the above-mentioned patent applications are MPC-type regulation systems or model-based predictive control systems, where the regulation of the delivered insulin dose takes into account a prediction of the future trend of the patient's blood glucose, obtained from a physiological model describing the assimilation of insulin by the patient's body and its impact on the patient's blood glucose, are here more particularly considered.

More particularly, many automated blood glucose control systems take into account a patient's blood glucose history, meal history, and insulin injection history to determine insulin doses to be delivered to the patient to maintain his/her blood glucose within a desired range.

In automated blood glucose control systems, a parameter which plays an essential role in the determination of the insulin doses to be delivered to the patient is the patient's insulin sensitivity factor, also called compensation sensitivity ratio, or compensation ratio, that is, the quantity of insulin necessary to lower the blood glucose by one gram per liter (in UI/g/l—where UI designates an international insulin unit, that is, the biological equivalent of approximately 0.0347 mg of human insulin).

A problem which is posed is that the insulin sensitivity factor may vary significantly from one patient to another, or, for a same patient, according to the patient's conditions (blood glucose level, physical activity, nycthemeral rhythm, stress, etc.).

In practice, known automated blood glucose control systems are based on a fixed insulin sensitivity factor, for example provided by the patient's diabetologist. Short-term variations of the factor are thus not taken into account. As a result, the quantities of insulin injected to the patient are sometimes inadequate, causing a risk of hyperglycemia or of hypoglycemia.

Patent applications US2010/0198520, US2013/0211220, and WO2017/040927 describe examples of methods of determination of a patient's insulin sensitivity factor taking into account his/her blood glucose history, insulin sensitivity factor, and meal history. Such methods are however relatively complex to implement and require having a data history over a relatively long past observation period. In particular, such methods do not enable to adjust the real time insulin sensitivity factor according to the variations of the patient's situation.

SUMMARY

Thus, an embodiment provides an automated system for controlling a patient's blood glucose, including a blood glucose sensor and a processing and control unit, wherein the processing and control unit is configured to calculate, from a first mathematical model $f_{CR}$ specific to the patient and taking into account a single blood glucose value $G^r$ measured by the sensor, a factor CR representative of the patient's insulin sensitivity.

According to an embodiment, the system further comprises an insulin injection device, wherein the processing and control unit is configured to control the insulin injection device by taking into account factor CR.

According to an embodiment, the processing and control unit is configured to predict, from a second mathematical model, the future trend of the patient's blood glucose over a prediction period, and to control the insulin injection device by taking the prediction into account.

According to an embodiment, the first mathematical model is a function of equation $$CR = f_{CR}(G^r) = a \times G^{rb} + c$$

where a, b, and c are parameters specific to the patient.

According to an embodiment, the processing and control unit is configured to implement a step of automatic calibration of first model $f_{CR}$ by taking into account a history of the blood glucose measured by the sensor, a history of insulin injected to the patient, and a history of carbohydrate ingestion by the patient over a past observation period.

According to an embodiment, the processing and control unit is configured to, during the automatic calibration step, measure a plurality of values of the patient's real insulin sensitivity factor $CR^r$ during a plurality of measurement events contained within the past observation period.

According to an embodiment, each measurement event corresponds to a continuous time range from an initial time $t_{init}$ to a final time $t_{final}$, complying with the following criteria:
- time $t_{init}$ is in a hyperglycemia phase, that is, a phase where the patient's blood glucose is greater than a predetermined threshold;
- a correction bolus, that is, an insulin dose, has been delivered to the patient after the beginning of the hyperglycemia phase and before time $t_{init}$, to limit the duration of the hyperglycemia phase;
- the patient's blood glucose continuously decreases between initial time $t_{init}$ and final time $t_{final}$;
- no carbohydrate ingestion by the patient has occurred between time $t_{init} - T_j$ and time $t_{final}$, where $T_j$ is a predetermined fasting duration.

According to an embodiment, the processing and control unit is configured to, during the automatic calibration step, determine the first mathematical model $f_{CR}$ by regression from said plurality of values of the real insulin sensitivity factor $CR^r$.

According to an embodiment, the processing and control unit is configured to, during an initial phase $T_{pop}$ of use of the system preceding the step of automatic calibration of the first model, use a non-personalized generic mathematical model $f_{CR-pop}$ to calculate factor CR.

According to an embodiment, the processing and control unit is configured to, during an intermediate phase $T_{hyb}$ of use of the system, subsequent to the initial phase $T_{pop}$ and preceding the step of automatic calibration of the first model, use a partially personalized mathematical model $f_{CR-hyb}$ to calculate factor CR.

According to an embodiment, the partially personalized mathematical model is defined by equation:

$$f_{CR-hyb}(G^r)=k\times f_{CR-pop}(G^r)$$

where k is a factor specific to the patient defined according to the following formula:

$$k = \frac{TDD_{moy}}{a1\times BW}$$

where BW designates the patient's weight, $TDD_{moy}$ designates the average daily insulin dose injected to the patient over period $T_{pop}$, and a1 is a constant factor in the range from 0.5 to 0.9.

According to an embodiment, the processing and control unit is configured to, after the step of automatic calibration of first model $f_{CR}$, implement a plurality of successive steps of re-calibration of the first model to take into account new data of blood glucose measured by the sensor, of insulin injected to the patient, and of carbohydrate ingestion by the patient.

BRIEF DESCRIPTION OF THE DRAWINGS

The foregoing features and advantages, as well as others, will be described in detail in the following description of specific embodiments given by way of illustration and not limitation with reference to the accompanying drawings, in which.

DETAILED DESCRIPTION

Figure 1:
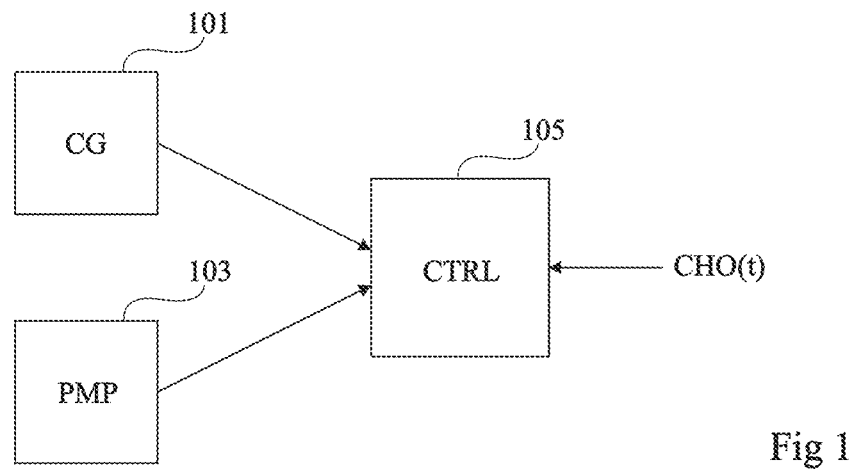
FIG. 1 schematically shows in the form of blocks an example of an automated system for regulating a patient's blood glucose according to an embodiment.

The same elements have been designated with the same reference numerals in the various drawings and, further, the various drawings are not to scale. For the sake of clarity, only the elements that are useful for an understanding of the embodiments described herein have been illustrated and described in detail. In particular, the hardware forming of the control and processing unit of the described systems has not been detailed, the forming of such a control and processing unit being within the abilities of those skilled in the art based on the functional indications of the present description. Further, the blood glucose measurement unit and the insulin injection device of the described systems have not been detailed, the described embodiment being compatible with all or most known blood glucose measurement and insulin injection devices. Unless specified otherwise, the terms "approximately", "substantially", and "in the order of" signify within 10%, preferably within 5%, of the value in question.

FIG. 1 schematically shows in the form of blocks an embodiment of an automated system of regulation of a patient's blood glucose.

The system of FIG. 1 comprises a sensor 101 (CG) capable of measuring the patient's blood glucose. In normal operation, sensor 101 may be permanently positioned on or inside of the patient's body, for example, at the level of his/her abdomen. Sensor 101 is for example a CGM-type ("Continuous Glucose Monitoring") sensor, that is, a sensor capable of continuously measuring (for example, at least once every five minutes) the patient's blood glucose. Sensor 101 is for example a subcutaneous glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of his/her abdomen.

The system of FIG. 1 further comprises a processing and control unit 105 (CTRL) connected on the one hand to blood glucose sensor 101, for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data CHO(t) representative of the time variation of the quantity of carbohydrates ingested by the patient.

Processing and control unit 105 is capable of determining the insulin doses to be injected to the patient by taking into account, in particular, the history of the blood glucose measured by sensor 101, the history of the insulin injected by device 103, and the history of carbohydrate ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smartphone-type device configured to implement a regulation method of the type described hereafter.

In the example of FIG. 1, processing and control unit 105 is capable of determining the quantity of insulin to be delivered to the patient by taking into account a prediction of the future trend of his/her blood glucose over time. More particularly, processing and control unit 105 is capable, based on the injected insulin history and on the ingested carbohydrate history, and based on a mathematical model, for example, a physiological model describing the assimilation of insulin by the patient's body and its impact on blood glucose, of determining a curve representative of the expected time trend of the patient's blood glucose, over a period to come called prediction period or prediction horizon, for example, a period from 1 to 10 hours. Taking this curve into account, processing and control unit 105 determines the insulin doses to be injected to the patient during the prediction period to come, so that the patient's real blood glucose (as opposed to the blood glucose estimated based on the physiological model) remains within acceptable limits, and in particular to limit risks of hyperglycemia or of hypoglycemia.

Figure 2:
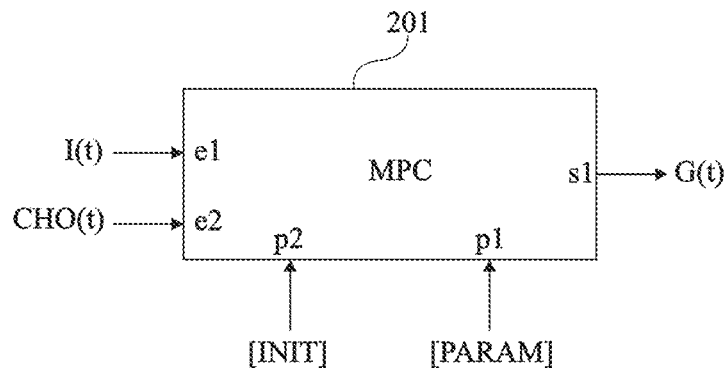
FIG. 2 is a simplified representation of a physiological model used in the system of FIG. 1 to predict the future trend of the patient's blood glucose.

FIG. 2 is a simplified representation of a mathematical model 201 (MPC) used in the system of FIG. 1 to predict the future trend of the patient's blood glucose. In FIG. 2, the model is shown in the form of a processing block comprising:

- an input e1 having a signal I(t) representative of the variation, over time t, of the quantity of insulin injected to the patient, applied thereto;
- an input e2 having a signal CHO(t) representative of the trend, over time t, of the quantity of carbohydrates ingested by the patient, applied thereto; and
- an output s1 supplying a signal G(t) representative of the variation, over time t, of the patient's estimated blood glucose.

Mathematical model 201 is for example a physiological model. As an example, model 201 is a compartmental model comprising, in addition to input variables I(t) and CHO(t) and output variable G(t), a plurality of state variables corresponding to physiological variables of the patient, varying over time. The time variation of the state variables and of output variable G(t) is ruled by a differential equation system comprising a plurality of parameters represented in FIG. 2 by a vector [PARAM] applied to an input p1 of block 201. The response of the physiological model is further conditioned by the initial states or initial values assigned to the state variables, represented in FIG. 2 by a vector [INIT] applied to an input p2 of block 201.

As an example, the physiological model 201 used in the system of FIG. 1 is the model called Hovorka model, described in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002). More generally, any other physiological model describing the assimilation of insulin by a patient's body and its effect on the patient's blood glucose may be used.

Among the parameters of vector [PARAM], some may be considered as constant for a given patient. Other parameters, called time-dependent parameters hereafter, are however capable of varying over time. Due to the variability of certain parameters of the system, it is in practice necessary to regularly recalibrate the model used, for example, every 1 to 20 minutes, for example, every 5 minutes, to make sure that the predictions of the model remain relevant. Such an update of the model, called model personalization, should be capable of being automatically carried out by the system of FIG. 1, that is, without requiring physically measuring the time-dependent parameters of the system on the patient and then transmitting them to processing and control unit 105.

Figure 3:
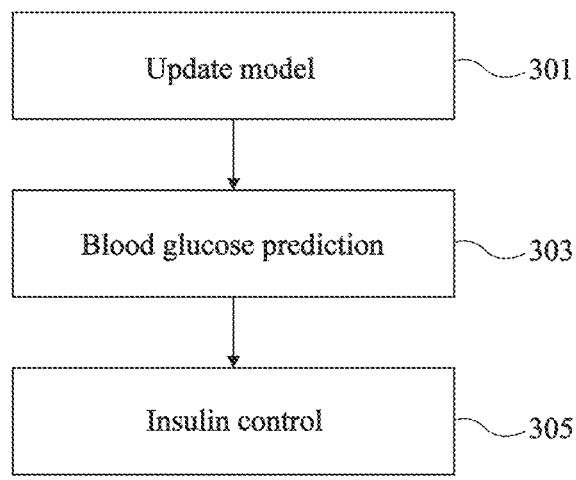
FIG. 3 is a diagram illustrating an example of an automated blood glucose regulation method capable of being implemented by the system of FIG. 1.

FIG. 3 is a diagram illustrating an example of an automated blood glucose regulation method capable of being implemented by the system of FIG. 1.

This method comprises a step 301 of recalibration or update of the model, which may for example be repeated at regular intervals, for example, every 1 to 20 minutes. During this step, processing and control unit 105 implements a method of re-estimation of the time-dependent parameters of the model by taking into account the data relative to the insulin effectively injected by device 103 and the data relative to the real blood glucose measured by sensor 101 for a past observation period of duration $\Delta T$, for example a period from 1 to 10 hours preceding the calibration step. More particularly, during the calibration step, processing and control unit 105 simulates the patient's behavior over the past observation period based on the physiological model (taking into account possible carbohydrate ingestions and insulin injections during this period) and compares the curve of the blood glucose estimated by the model with the curve of the real blood glucose measured by the sensor during this same period. Processing and control unit 105 then searches, for the time-dependent parameters of the model, a set of values leading to minimizing a quantity representative of the error between the blood glucose curve estimated by the model and the real blood glucose curve measured by the sensor during the observation period. As an example, the processing and control unit searches for a set of parameters leading to minimizing an indicator m representative of the area between the curve of the blood glucose estimated by the model and the curve of the real blood glucose measured by the sensor during the observation period, also called standard deviation between the estimated glucose and the real glucose, for example defined as follows:

$$m = \frac{1}{\Delta T}\sum_{t=t_0-\Delta T}^{t_0} |G^r(t) - G(t)|^2 \qquad \text{(eq 1)}$$

where t is a discretized time variable, $t_0-\Delta T$ corresponds to the time of beginning of the past observation phase, $t_0$ corresponds to the end time of the past observation phase (for example corresponding to the time of beginning of the model calibration step), $G^r$ is the curve of time variation of the real blood glucose measured by sensor 101 during period $[t_0-\Delta T, t_0]$, and G is the curve of the blood glucose estimated based on the model during period $[t_0-\Delta T, t_0]$. As a variant, for the calculation of the mean standard deviation, variable $\Delta T$ may be replaced with the number of measurements performed during the past observation period. The optimal parameter search algorithm used during this step is not detailed in the present application, the described embodiments being compatible with usual algorithms used in various field to solve problems of parameter optimization by minimization of a cost function.

It should be noted that during step 301, in addition to the time-dependent parameters of the model, processing and control unit 105 defines a vector [INIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period $[t_0-\Delta T, t_0]$ having the model calibration based thereon, the patient was in a stationary state, with a constant injected insulin flow, and no dietary intake of carbohydrates. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, but adding the constraint that the blood glucose estimated at time $t_0-\Delta T$ is equal to the real blood glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 3 further comprises, after step 301, a step 303 of prediction, by processing and control unit 105, of the time variation of the patient's blood glucose over a prediction period to come [t0, $t_0+T_{pred}$] of duration $T_{pred}$, for example, in the range from 1 to 10 hours, based on the physiological model updated at step 301 and taking into account the history of the insulin injected to the patient and the history of carbohydrates ingested by the patient.

The method of FIG. 3 further comprises, after step 303, a step 305 of determination, by processing and control unit 105, by taking into account the future blood glucose curve predicted at step 303, of the insulin doses to be injected to the patient for the prediction period to come [t0, $t_0+T_{pred}$]. At the end of this step, processing and control unit 105 may program injection device 103 to deliver the doses determined during prediction period [t0, $t_0+T_{pred}$].

Steps 303 of prediction of the blood glucose and 305 of determination of the future doses of insulin to be delivered may for example be repeated at each update of the physiological model (that is, after each iteration of step 301), for each new carbohydrate ingestion notified by the patient, and/or for each new administration of an insulin dose by injection device 103.

According to an aspect of an embodiment, during step 305, processing and control unit 105 estimates the patient's insulin sensitivity factor CR based on a single blood glucose value measured by sensor 101, from a predetermined mathematical model. In other words, during step 305, processing and control unit 105 calculates the patient's insulin sensitivity factor CR based on a predetermined mathematical function $f_{CR}$ such that $CR=f_{CR}(G^r(t))$, where $G^r(t)$ is the real value of the patient's blood glucose measured by sensor 101 at a current time t, for example, at time $t=t_0$. During step 305, processing and control unit 105 then determines the future insulin doses to be delivered to the patient by taking into account the sensitivity factor CR thus calculated.

The inventors have shown that there exists, for a given patient, a strong correlation between the time variation of the patient's blood glucose and the time variation of the patient's insulin sensitivity factor. The inventors have particularly shown that the real time adjustment of the patient's insulin sensitivity factor according to his/her instantaneous blood glucose enables to determine with a better accuracy the future insulin doses to be delivered to the patient and thus to limit risks of hyperglycemia or hypoglycemia.

Figure 4A:
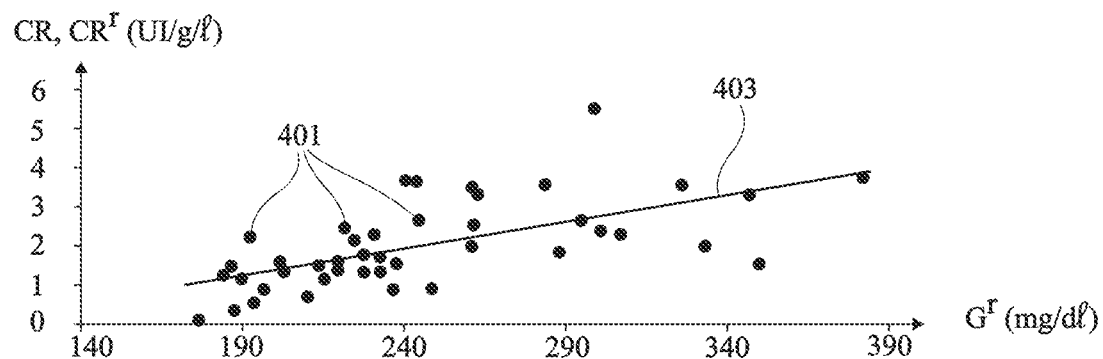
FIGS. 4A and 4B are diagrams representing the variation of a patient's insulin sensitivity factor according to his/her blood glucose.
Figure 4B:
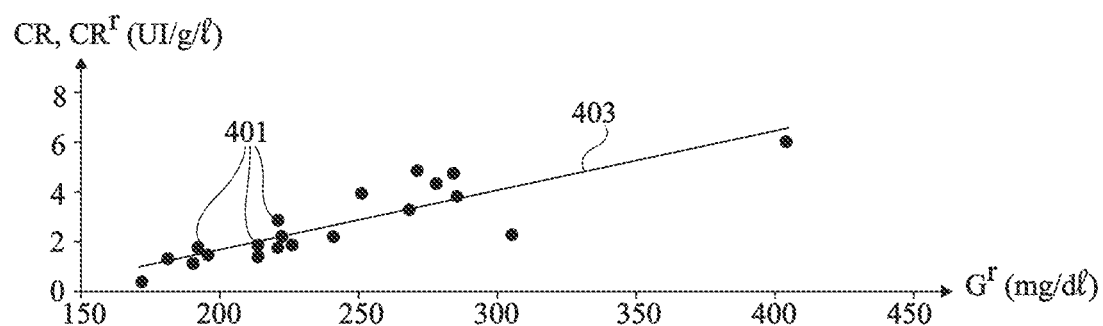

FIGS. 4A and 4B are diagrams respectively showing, for two different patients, the variation of the patient's insulin sensitivity (in ordinates, in UI/g/l) according to his/her blood glucose (in abscissas, in mg/dl). Each diagram comprises a plurality of points 401, each corresponding to a measurement of the patient's real insulin sensitivity factor $CR^r$ and to a corresponding measurement (that is, correlated in time) of the patient's real blood glucose $G^r$.

The real insulin sensitivity factor $CR^r$ may be measured by any known method of measurement of a patient's insulin sensitivity factor, for example, by methods of the type described in above-mentioned patent applications US2010/0198520, US2013/0211220, and WO2017/040927.

In a preferred embodiment, the patient's real insulin sensitivity factor $CR^r$ is determined from the patient's blood glucose history (for example, measured by sensor 101 in the system of FIG. 1), meal history, and insulin injection history, according to the following method.

Based on the patient's data history, measurement events are identified, that is, time ranges during which the insulin sensitivity factor is isolated, that is, during which a decrease in the patient's blood glucose linked to the delivery of insulin can be observed. As an example, the selected events are continuous time ranges from an initial time $t_{init}$ to a final time $t_{final}$, complying with the following criteria:

time $t_{init}$ is in a hyperglycemia phase, that is, a phase where the patient's blood glucose is greater than a predetermined threshold, for example, in the order of 1.40 g/l;

a correction bolus, that is, an additional insulin dose, has been delivered to the patient after the beginning of the hyperglycemia phase and before time $t_{init}$, to limit the duration of the hyperglycemia phase;

the patient's blood glucose continuously decreases between initial time $t_{init}$ and final time $t_{final}$;

no carbohydrate ingestion by the patient has occurred between time $t_{init}-T_j$ and time $t_{final}$, where $T_j$ is a predetermined fasting period, for example, longer than or equal to 1 hr and preferably longer than or equal to 2 hrs.

As an example, time $t_{init}$ corresponds to the blood glucose peak of the hyperglycemia phase. Time $t_{final}$ for example corresponds to a time of blood glucose stabilization or rise following the hyperglycemia phase, or also to a disturbance such as a meal or a carbohydrate ingestion.

For each identified event, the patient's real insulin sensitivity $CR^r$ is calculated as follows:

$$CR^r = \Delta I / \Delta G,$$

where $\Delta I$ designates the quantity of insulin consumed during the event and $\Delta G$ designates the difference between the patient's real blood glucose at time $t_{init}$ of beginning of the event and the patient's real blood glucose at time $t_{final}$ of end of the event. The quantity of insulin $\Delta I$ consumed during the event may for example be calculated by taking into account the insulin doses delivered before and after the event, and the kinetics of insulin absorption by the body. As an example, the quantity of insulin $\Delta I$ consumed during the event corresponds to the difference between the patient's quantity of insulin on board, that is, the quantity of insulin still active (that is, still capable of having an effect of the blood glucose), at time $t_{init}$ of beginning of the event and the quantity of insulin on board at time $t_{final}$ of end of the event. The determination of the patient's quantity of insulin on board at times $t_{init}$ and $t_{final}$ may be performed by any known method of determination of a patient's quantity of insulin on board. As an example, the determination of the patient's quantity of insulin on board at a time t may be calculated by convolution, over a period from a time preceding time t to time t, of a curve representative of the time variation of the quantity of insulin injected to the patient before time t, and of a function $f_{IOB}$ representative of the kinetics of insulin consumption by the body, for example, function $$f_{IOB}(t) = \left(1 + \frac{t-1}{\tau}\right) * e^{-\frac{t-1}{\tau}},$$

where t is a discretized time variable and t is a time constant of predetermined duration, for example, in the range from 40 to 60 minutes, for example, in the order of 47 minutes.

For each event, the retained value of the patient's real blood glucose is for example the real blood glucose value $G^r(t_{init})$ at time $t_{init}$ of beginning of the event.

For each patient, to define a function or a mathematical model $f_{CR}$ specific to the patient, a relatively high number of events $Nb_{ev}$ is first identified in the patient's history data, and, for each event, a value of the insulin sensitivity factor $CR^r$ and an associated blood glucose value $G^r$ are measured. As an example, the number of events $Nb_{ev}$ used to define function $f_{CR}$ is in the range from 20 to 100, for example, between 30 and 60, for example, in the order of 40. In practice, a data history from several weeks to several months may be necessary to obtain the number $Nb_{ev}$ of desired measurements. Function $f_{CR}$ is then determined by regression from the $Nb_{ev}$ measurement points specific to the patient (the points 401 of FIGS. 4A and 4B). As an example, for each patient, function $f_{CR}$ is obtained by regression from the $Nb_{ev}$ measurement points 401 obtained for the patient. For each patient, function $f_{CR}$ then is a function of equation:

$$f_{CR}(G^r) = a \times G^{rb} + c$$

where a, b, and c are parameters specific to the patient, parameter b corresponding to the order of the model. As an example, parameter b is set to be equal to 1, the model then being a linear model.

On each of the diagrams of FIGS. 4A and 4B, a line 403 represents the function $f_{CR}$ determined for the patient, linking the patient's blood glucose $G^r$ to his/her insulin sensitivity factor CR.

As an example, in the system of FIG. 1, function $f_{CR}$ may be determined in automated fashion by processing and control unit 105, during a calibration phase.

Control and processing unit 105 may further be configured to update in automated fashion, for example, periodically, the parameters of function $f_{CR}$, to take into account the new history data recorded by the regulation system along its use by the patient.

In a preferred embodiment, the number $Nb_{ev}$ of events taken into account for each update of the parameters of function $f_{CR}$ remains constant. In other words, each time a new event is taken into account for the update of the parameters of function $f_{CR}$, a previous event, for example, the oldest event, is excluded from the model, which enables for the model not to set and to be able to evolve over time.

During model update phases, the measurements which would result in a significant modification of the model are preferably excluded, so that abnormal or exceptional events do not result in an instability of the model.

As an example, every day, control and processing unit 105 may perform one or a plurality of new measurements of the patient's real insulin sensitivity factor $CR^r$, and decide whether to incorporate or not such measurements, according to whether or not they comply with predetermined conditions.

As an example, each new measurement of the patient's real insulin sensitivity factor $CR^r$ is incorporated to the model only if it complies with the following conditions:

the interval between the new measurement of the real insulin sensitivity factor $CR^r$ and the value of the insulin sensitivity factor CR estimated from the current model (for a same blood glucose value $G^r$) is smaller, in absolute value, than the standard deviation of all the values of factor $CR^r$ taken into account in the current model; and the variation of each of the parameters of model $f_{CR}$ (parameters a and b in the above-mentioned example) linked to the incorporation of the new measurement of factor $CR^r$ is smaller than a predetermined threshold, for example smaller than a predetermined percentage P, for example in the range from 1 to 20%, of the value of the parameter before the update of the model.

Processing and control unit 105 may further be configured to, after each use by the regulation system of a value of the insulin sensitivity factor CR estimated from model $f_{CR}$, verify the relevance of the model and, if necessary, correct the model. More particularly, after each use of a value of the insulin sensitivity factor CR estimated from model $f_{CR}$ to correct a hyperglycemia (that is, to determine an insulin bolus to be injected to the patent to correct the hyperglycemia), processing and control unit 105 can calculate the patent's real insulin sensitivity factor $CR^r$ over a past observation period contained in the phase of decrease of the patient's glycemia following the hyperglycemia peak, and then calculate error $\varepsilon = CR^r - CR$ between the real insulin sensitivity factor and the estimated insulin sensitivity factor. Processing and control unit 105 can then multiply error e by a cost function, for example, the function described in the article entitled "Adaptive control in an artificial pancreas for people with type 1 diabetes" of D. Boiroux et al. (J. B. (2017)—Control Engineering Practice, 58, 332-342), and then compare the result of the multiplication with a predetermined threshold to estimate whether the model is relevant or not. If the model is considered non-relevant, the model may be corrected for a future use.

Processing and control unit 105 may further be configured to estimate the relevance of the model during an event, for example after a predetermined period, for example, in the range from 30 to 90 minutes, starting from the injection of a correction bolus after the detection of a hyperglycemia. Processing and control unit 105 may for example measure the real insulin sensitivity factor $CR^r$ over the considered period, and determine the sign of error e between the real insulin sensitivity factor $CR^r$ and the estimated insulin sensitivity factor CR. According to the sign of error e, processing and control unit 105 may order an additional insulin injection, or decrease the insulin doses to be injected programmed for a period to come, or also offer the patient a glucose administration (carbohydrate ingestion) if the estimated factor CR seems too high.

Figure 5:
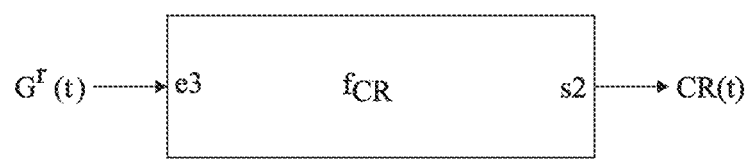
FIG. 5 is a simplified representation of a mathematical model used in the system of FIG. 1 to determine the patient's insulin sensitivity factor.

FIG. 5 is a simplified representation of the mathematical model $f_{CR}$ used in the system of FIG. 1 to determine the patient's insulin sensitivity factor. In FIG. 5, the model is shown in the form of a processing block comprising an input e3 having a signal $G^r(t)$ representative of the patient's real blood glucose, measured by sensor 101, at a measurement time t, applied thereto, and an output s2 supplying a signal CR(t) representative of the patient's insulin sensitivity factor at time t.

Figure 6:
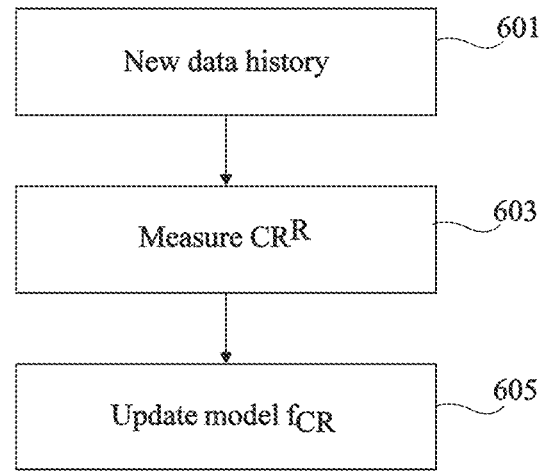
FIG. 6 is a diagram illustrating an example of a method capable of being implemented by the system of FIG. 1 to update the mathematical model of FIG. 5.

FIG. 6 is a diagram illustrating an example of a method capable of being implemented by the system of FIG. 1 to update mathematical model $f_{CR}$ so as to take into account a new data history of the patient.

The method of FIG. 6 comprises a step 601 during which processing and control unit 105 acquires and stores the real blood glucose data $G^r$ measured by sensor 101, the data of insulin effectively injected by device 103, and the data of carbohydrate ingestion by the patient, over an observation period. The observation period considered at step 601 is selected to comprise at least one event enabling to measure the patient's real sensitivity factor $CR^r$.

The method of FIG. 6 further comprises, after step 601, a step 603 of calculation of the patient's real insulin sensitivity factor $CR^r$ based on the data acquired during the observation period.

The method of FIG. 6 further comprises, after step 603, a step 605 of update of model $f_{CR}$, taking into account the new value of the real insulin sensitivity factor $CR^r$ determined at step 603.

As previously indicated, a data history over a relatively long period, typically from several weeks to several months, is necessary to be able to define a model $f_{CR}$ specific to a given patient.

At the beginning of the use of the regulation system, before a sufficiently significant data history has been acquired, a generic model (that is, not specific to the patient) $f_{CR\text{-}pop}$, also called population model, may be used to calculate in real time the patient's insulin sensitivity factor according to his/her blood glucose. As an example, model $f_{CR\text{-}pop}$ is determined from a database containing the blood glucose history, the insulin injection history, and the carbohydrate intake history of a large number of patients, for example, at least 20 patients, over a relatively long period, for example, from several weeks to several months. For each patient, a plurality of events are identified, and for each event, a value of the patient's insulin sensitivity factor $CR^r$, and a corresponding blood glucose value $G^r$ are determined, for example, identically or similarly to what has been previously described in relation with FIGS. 4A and 4B. For each measured value of the insulin sensitivity factor $CR^r$, factor $CR^r$ is normalized by the patient's weight. In other words, a factor $CRBW^r = CR^r/BW$ is calculated, where BW designates the patient's weight. Thus, for each patient, a plurality of couples of values $(CRBW^r, G^r)$ are determined. Model $f_{CR\text{-}pop}$ is then determined by regression from the set of determined couples of values $(CRBW^r, G^r)$, all patients being confounded. As an example, model $f_{CR\text{-}pop}$ is determined by regression from the set of determined couples of values $(CRBW^r, G^r)$.

Figure 7:
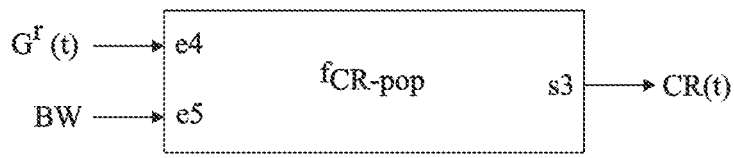
FIG. 7 is a simplified representation of another example of a mathematical model used in the system of FIG. 1 to determine the patient's insulin sensitivity factor.

FIG. 7 is a simplified representation of the mathematical model $f_{CR\text{-}pop}$ used in the system of FIG. 1 during an initial phase of use of the system, before a data history sufficiently significant to determine a model specific to the patient has been acquired. In FIG. 7, the model is represented in the form of a processing block comprising an input e4 having a signal $G^r(t)$ representative of the patient's real blood glucose, measured by sensor 101, at a measurement time t, applied thereto, an input e5 having a value representative of the patient's weight BW, for example, in kg, applied thereto, and an output s3 supplying a signal $CR(t) = BW \times f_{CR\text{-}pop}(G^r(t))$, representative of the patient's insulin sensitivity factor at time t.

For identical weights and identical blood glucose, two patients however do not necessarily have the same insulin sensitivity factor. Thus, it is desirable to personalize the model as fast as possible, as soon as a sufficient quantity of history data has been acquired.

In a preferred embodiment, between the initial phase where the above-defined generic model $f_{CR\text{-}pop}$ is used, and a steady-state phase where a model $f_{CR}$ specific to the patient is used, it is provided to use a hybrid model $f_{CR\text{-}hyb}$, defined as follows.

Model $f_{CR\text{-}hyb}$ is defined after a certain period $T_{pop}$ of use of the regulation system based on population model $f_{CR\text{-}pop}$, for example, a period from 1 to 7 days, for example, a period in the order of 3 days. At the end of period $T_{pop}$, processing and control unit 105 calculates a factor k specific to the patient according to the following formula:

$$k = \frac{TDD_{moy}}{a1 * BW}$$

where BW designates the patient's weight, $TDD_{moy}$ designates the average daily insulin dose injected to the patient over period $T_{pop}$, and a1 is a constant factor in the range from 0.5 to 0.9. Hybrid model $f_{CR\text{-}hyb}$ is then defined as follows:

$$f_{CR\text{-}hyb} = k * f_{CR\text{-}pop}$$

As a variant, factor k is calculated according to the following formula:

$$k = \frac{TDD_{basal}}{a2 * BW}$$

where $TDD_{basal}$ designates the daily basal insulin dose (that is, in the absence of any correction bolus) injected to the patient over period $T_{pop}$, and a2 is a constant factor, for example, in the range from 0.2 to 0.5.

Figure 8:
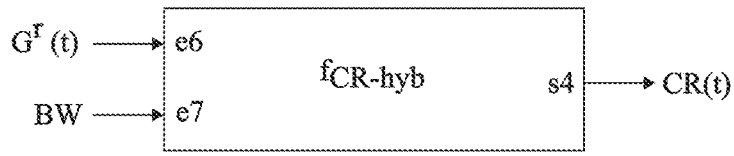
FIG. 8 is a simplified representation of another example of a mathematical model used in the system of FIG. 1 to determine the patient's insulin sensitivity factor.

FIG. 8 is a simplified representation of the mathematical model $f_{CR\text{-}hyb}$ used in the system of FIG. 1 during an intermediate phase $T_{hyb}$ of use of the system, after phase $T_{pop}$ and before a data history sufficiently significant to determine a model specific to the patient has been acquired. In FIG. 8, the model is shown in the form of a processing block comprising an input e6 having a signal $G^r(t)$ representative of the patient's real blood glucose, measured by sensor 101, at a measurement time t, applied thereto, an input e7 having a value representative of the patient's weight BW, for example, in kg, applied thereto, and an output s4 supplying a signal $$CR(t) = BW \times f_{CR\text{-}hyb}(G^r)(t)) = k \times BW \times f_{CR\text{-}pop}(G^r(t))$$

representative of the patient's insulin sensitivity factor at time t.

Figure 9:
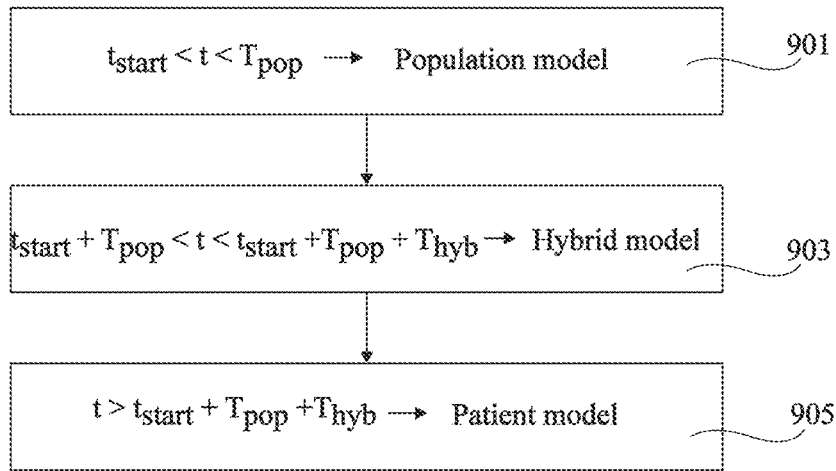
FIG. 9 is a diagram illustrating an example of a method of controlling of a patient's blood glucose capable of being implemented by the system of FIG. 1.

FIG. 9 is a diagram schematically illustrating an example of a method of controlling a patient's blood glucose capable of being implemented by the system of FIG. 1. A method where the patient's insulin sensitivity factor CR is successively estimated a plurality of times from a mathematical model by taking into account, for each estimate, a single blood glucose value measured by blood glucose sensor 101 of the system, is here considered.

During an initial phase 901 of duration $T_{pop}$, ranging from an initial time $t_{start}$ of beginning of use of the regulation system by the patient to time $t_{start} + T_{pop}$, processing and control unit 105 uses population model $f_{CR\text{-}pop}$ to estimate the patient's insulin sensitivity factor CR. At the end of phase 901, processing and control unit 105 determines a partially personalized model $f_{CR\text{-}hyb}$ based on the data acquired during phase 901.

During an intermediate phase 903 of duration $T_{hyb}$, ranging from time $t_{start}+T_{pop}$ to time $t_{start}+T_{pop}+T_{hyb}$, processing and control unit 105 uses hybrid model $f_{CR-hyb}$ to estimate the patient's insulin sensitivity factor CR. At the end of phase 903, processing and control unit 105 determines a model specific to the patient $f_{CR}$ based on the data acquired during phases 901 and 903.

During a steady state phase 905 subsequent to time $t_0+T_{pop}+T_{hyb}$, processing and control unit 105 uses patient model $f_{CR}$ to calculate the patient's insulin sensitivity factor CR. Processing and control unit 105 may further regularly update patient model $f_{CR}$ to take into account new data acquired for the patient.

Specific embodiments have been described. Various alterations and modifications will occur to those skilled in the art. In particular, the described embodiments are not limited to the specific example of a blood glucose regulation system described in relation with FIGS. 1 to 3, that is, a predictive control system using a mathematical model to predict the future trend of the patient's blood glucose and accordingly adjust the insulin doses to be delivered to the patient. More generally the provided method of real time estimation of the patient's insulin sensitivity factor CR, from a single blood glucose value measured on the patient, may be implemented in any blood glucose regulation system capable of taking advantage of an in situ and real time estimate of the patient's insulin sensitivity factor.

The invention claimed is:

1. An automated system for controlling a patient's blood glucose, comprising a blood glucose sensor and a processing and control unit, wherein the blood glucose sensor is configured to measure a blood glucose value ($G^r$) of the patient, and wherein the processing and control unit is configured to:
   determine, based on a history of blood glucose values measured by the blood glucose sensor, a history of insulin injected to the patient, and a history of carbohydrate ingestion by the patient, a plurality of real insulin sensitivity factor ($CR_r$) values for a plurality of events identified for the patient over a past observation period, wherein each event of the plurality of events corresponds to a continuous time range from an initial time ($t_{init}$) to a final time ($t_{final}$) during which the insulin sensitivity factor ($CR_r$) is isolated,
   calibrate a first mathematical model ($f_{CR}$) based on the plurality of real insulin sensitivity factor ($CR_r$) values, the calibrating comprising determining the first mathematical model ($f_{CR}$) by regression from the plurality of real insulin sensitivity factor ($CR_r$) values; and
   calculate, from the first mathematical model ($f_{CR}$) and taking into account the blood glucose value ($G^r$) measured by the blood glucose sensor, a factor (CR) representative of an insulin sensitivity of the patient.

2. The system according to claim 1, further comprising an insulin injection device, wherein the processing and control unit is configured to control the insulin injection device by taking into account the factor (CR) representative of the insulin sensitivity of the patient.

3. The system according to claim 2, wherein the processing and control unit is configured to predict, from a second mathematical model, a future trend of the patient's blood glucose over a prediction period, and to control the insulin injection device by taking the prediction into account.

4. The system according to claim 1, wherein the first mathematical model is a function of equation $$CR=f_{CR}(G^r)=a \times G^{rb}+c$$

where a, b, and c are parameters specific to the patient.

5. The system according to claim 1, wherein the continuous time range complies with the following criteria:
   the initial time ($t_{init}$) is in a hyperglycemia phase, that is, a phase where the patient's blood glucose is greater than a predetermined threshold;
   a correction bolus, that is, an additional insulin dose has been delivered to the patient after a beginning of the hyperglycemia phase and before the initial time ($t_{init}$), to limit a duration of the hyperglycemia phase;
   the patient's blood glucose continuously decreases between the initial time ($t_{init}$) and the final time ($t_{final}$);
   no carbohydrate ingestion by the patient has occurred between a time ($t_{init}-T_j$) and the final time ($t_{final}$), wherein the time ($t_{init}-T_j$) is the initial time ($t_{init}$) minus a predetermined fasting duration ($T_j$).

6. The system according to claim 1, wherein the processing and control unit is configured to, during an initial phase ($T_{pop}$) of use of the system prior to calibrating the first mathematical model, use a non-personalized generic mathematical model ($f_{CR-pop}$) to calculate the factor (CR) representative of the insulin sensitivity of the patient.

7. The system according to claim 6, wherein the processing and control unit is configured to, during an intermediate phase ($T_{hyb}$) of use of the system, subsequent to the initial phase ($T_{pop}$) and prior to calibrating the first mathematical model, use a partially personalized mathematical model ($f_{CR-hyb}$) to calculate the factor (CR) representative of the insulin sensitivity of the patient.

8. The system according to claim 7, wherein the partially personalized mathematical model is defined by equation:

$$f_{CR-hyb}(G^r)=k \times f_{CR-pop}(G^r)$$

where k is a factor specific to the patient defined according to the following formula:

$$k = \frac{TDD_{moy}}{a1 \times BW}$$

where BW designates a weight of the patient, $TDD_{moy}$ designates an average daily insulin dose injected to the patient over the initial phase ($T_{pop}$), and a1 is a constant factor in a range from 0.5 to 0.9.

9. The system according to claim 1, wherein the processing and control unit is configured to, after calibrating the first mathematical model ($f_{CR}$), implement a plurality of successive steps of re-calibration of the first mathematical model to take into account new data of blood glucose measured by the blood glucose sensor, of insulin injected to the patient, and of carbohydrate ingestion by the patient.

10. The system according to claim 1, further comprising an insulin injection device, wherein the processing and control unit is configured to regulate insulin delivered to the patient based on the determined factor JCR) representative of the insulin sensitivity of the patient, wherein the regulating comprises controlling the insulin injection device.

* * * * *